(12) United States Patent
Ning

(10) Patent No.: US 7,241,917 B2
(45) Date of Patent: Jul. 10, 2007

(54) 1-CALCIUM PHOSPHATE-URACIL AND METHOD FOR PREPARING THEREOF

(76) Inventor: Qizhi Ning, 19-33 Xiao jia cun si xiang, Chengdu (CN) 610031

( * ) Notice: Subject to any disclaimer, the term of this patent is extended or adjusted under 35 U.S.C. 154(b) by 358 days.

(21) Appl. No.: 10/865,095

(22) Filed: Jun. 10, 2004

(65) Prior Publication Data

US 2005/0277622 A1 Dec. 15, 2005

(51) Int. Cl.
*C07F 9/22* (2006.01)
(52) U.S. Cl. ............................................. 562/19
(58) Field of Classification Search ................ 562/19
See application file for complete search history.

(56) References Cited

U.S. PATENT DOCUMENTS 5,200,554 A * 4/1993 Nasman et al. ............... 562/21

\* cited by examiner

*Primary Examiner*—Joseph K. McKane
*Assistant Examiner*—Robert Shiao
(74) *Attorney, Agent, or Firm*—Dickstein, Shapiro, LLP.

(57) ABSTRACT

The present invention provides a compound of 1-calcium phosphate-uracil of the following structure. The compound can be a flavourless, white crystal or crystalline powder with a molecular weight of 216.2276

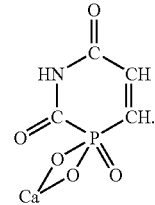

4 Claims, 2 Drawing Sheets 1-calcium phosphate-uracil 1-calcium phosphate-cytosine 1-calcium phosphate-thymine 9-calcium phosphate-guanine 9-calcium phosphate-adenine 9-calcium phosphate
-hypoxanthine AZT azidothymidine
zidovudine 3Tc lamivudine

1-CALCIUM PHOSPHATE-URACIL AND METHOD FOR PREPARING THEREOF

FIELD OF THE INVENTION

The present invention relates to uracil and uracil-derived medicament, in particularly medicament of 1-calcium phosphate-uracil.

BACKGROUND OF THE INVENTION

Uracil-derived medicaments of prior art are mono-type medicines and have a certain degree of side effect.

DISCLOSURE OF THE INVENTION

The objective of the present invention is to overcome disadvantage that one compound only works on one type of disease. The present invention provides a medicament of 1-calcium phosphate-uracil. The medicament has an efficacy on auto-selected targets. The medicament is used for treatment of both symptom and pathogenic factor of different diseases and improvement of immunity.

The present invention provides a medicament of 1-calcium phosphate-uracil having a structure of following formula:

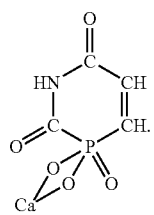

The 1-calcium phosphate-uracil is a flavourless, white crystal or crystalline powder with a molecular weight of 216.1276.

The present invention also provides a method for the preparation of the medicament of 1-calcium phosphate-uracil, comprising:

1. preparing phosphoric acid working solution: mixing 38.8–41.2 g of $Na_2HPO_4.12H_2O$ with 3.90–4.14 ml of 85% aqueous $H_3PO_4$ solution, controlling the pH of mixed solution to a range between 5.92 and 6.28;

2. adding 3.88–4.12 g uracil to 1164–1236 ml of said phosphoric acid working solution for dissolution, pouring obtained solution into reactor, disposing the reactor in a water tank of 38° C.–39° C. without contacting with water, adding 31.04–32.96 mg of creatine kinase, i.e. CPK with a code of 2.7.3.2, agitating for 60–70 minutes, incubating for 30–40 minutes at 38° C.–39° C., and standing at room temperature;

3. filtering the above solution with filter, pouring the all of 1130–1195 ml filtrate obtained into reactor, and disposing in a water tank of 38° C.–39° C.;

4. adding 41.71–44.29 ml of 4.8–5.2% aqueous $CaCl_2$ solution, agitating for 22–27 minutes, incubating at 38° C.–39° C., and standing at room temperature;

5. filtering the above material with clean silk cloth, discarding the filtrate, soaking in distilled water for 8–15 hours, drying, thus obtaining the medicament of 1-calcium phosphate-uracil as white crystal or crystalline powder.

The present invention also provides a method for treatment of viral infection, tumor, AIDS, fever, ache, and constipation, and improvement of immunity, kidney function, neural regulation and physical recovery, which comprises administrating the medicament of 1-calcium phosphate-uracil to patients.

The present invention also provides the use of the medicament of 1-calcium phosphate-uracil for treatment of viral infection, tumor, AIDS, fever, ache, and constipation, improvement of immunity, kidney function, neural regulation and physical recovery.

The present invention also provides 1-calcium phosphate-cytosine having a structure of following formula:

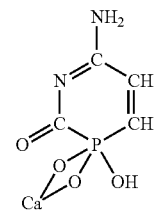

The present invention also provides a method for the preparation of 1-calcium phosphate-cytosine, comprising substituting position 1 of the pyrimidine with $H_3PO_4$.

The present invention also provides 1-calcium phosphate-thymine having a structure of following formula:

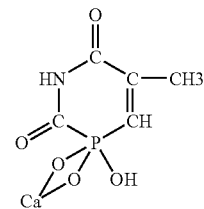

The present invention also provides a method for the preparation of 1-calcium phosphate-thymine, comprising substituting position 1 of the pyrimidine with $H_3PO_4$.

The present invention also provides 9-calcium phosphate-guanine having a structure of following formula:

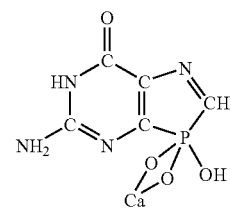

The present invention also provides a method for the preparation of 9-calcium phosphate-guanine, comprising substituting position 9 of the purine with $H_3PO_4$.

The present invention also provides 9-calcium phosphate-adenine having a structure of following formula:

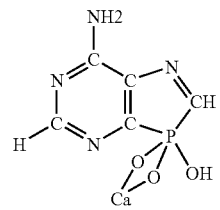

The present invention also provides a method for the preparation of 9-calcium phosphate-adenine, comprising substituting position 9 of the purine with $H_3PO_4$.

The present invention also provides 9-calcium phosphate-hypoxanthine having a structure of following formula:

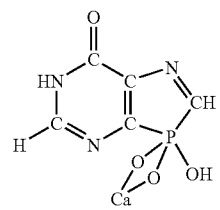

The present invention also provides a method for the preparation of 9-calcium phosphate-hypoxanthine, comprising substituting position 9 of the purine with $H_3PO_4$.

The medicament of 1-calcium phosphate-uracil has an efficacy on auto-selected target. It improves immunity and has a broad therapeutic spectrum.

The medicament selectively works on target by self-catalysis and self-assemble effect of high energy phosphate, thus achieves broad-spectrum and safe therapeutic effect.

In particularly, the medicament has following effects:
1. significant effect of anti-viral infection;
2. improvement of immunity and kidney function;
3. anti-AIDS effect (based on structure illation). It has significantly synergic effect when in combination with anti-AIDS drugs (AZT) azidothymidine zidovudine and (3Tc) lamivudine alternatively. FIG. 7 shows Structure formula of anti-AIDS drug AZT azidothymidine zidovudine of prior art and FIG. 8 shows Structure formula of anti-AIDS drug 3Tc lamivudine of prior art.
4. anti-tumor;
5. functions of neural regulation, abatement of fever, analgesic and treatment of constipation;
6. without drug dependence and adverse effect.

EXAMPLES

Example 1

Figure 1:
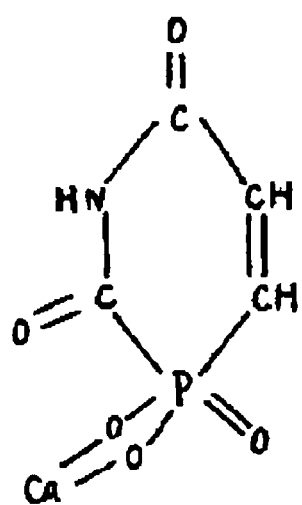
FIG. 1 shows structure formula of 1-calcium phosphate-uracil.

A Method for the Preparation of the Medicament of 1-Calcium Phosphate-Uracil, Comprising Following Steps:

1. phosphoric acid working solution was prepared: 38.8 g of $Na_2HPO_4 \cdot 12H_2O$ was mixed with 3.90 ml of 85% aqueous $H_3PO_4$ solution, the pH of mixed solution was controlled to 5.92;

2. 3.88 g uracil was added to 1164 ml of said phosphoric acid working solution for dissolution, obtained solution was poured into reactor, the reactor was disposed in a water tank of 38° C. without contacting with water, 31.04 mg of creatine kinase, i.e. CPK with a code of 2.7.3.2 was added, agitated at 115–125 rpm for 60 minutes, incubated for 30 minutes, and standed at room temperature for 50–70 minutes;

3. the above solution was filtered with filter, the all of 1132 ml filtrate obtained was poured into reactor, and disposed in a water tank of 38° C.;

4. 41.71 ml of 4.8% aqueous $CaCl_2$ solution was added, agitated at 165–180 rpm for 13–17 minutes, then agitated at 110–120 rpm for 7–9 minutes and stopping, incubated for 38 minutes, and standed at room temperature for 70 minutes;

5. the above material was filtered with clean silk cloth, discarded the filtrate, soaked in distilled water for 8 hours, dried at 55° C. for 20 hours to obtain 2.1065 g medicament of 1-calcium phosphate-uracil as white crystal or crystalline powder. The structure formula of medicament is showed in FIG. 1.

Example 2

A Method for the Preparation of the Medicament of 1-calcium Phosphate-uracil, Comprising Following Steps 1. phosphoric acid working solution was prepared: 41.2 g of $Na_2HPO_4 \cdot 12H_2O$ was mixed with 4.14 ml of 85% aqueous $H_3PO_4$ solution, the pH of mixed solution was controlled to 6.28;

2. 4.12 g uracil was added to 1236 ml of said phosphoric acid working solution for dissolution, obtained solution was poured into reactor, the reactor was disposed in a water tank of 39° C. without contacting with water, 32.96 mg of creatine kinase, i.e. CPK with a code of 2.7.3.2 was added, agitated at 115–125 rpm for 70 minutes, incubated for 40 minutes, and standed at room temperature for 50–70 minutes;

3. the above solution was filtered with filter, the all of 1198 ml filtrate obtained was poured into reactor, and disposed in a water tank of 39° C.;

4. 44.29 ml of 5.2% aqueous $CaCl_2$ solution was added, agitated at 165–180 rpm for 13–17 minutes, then agitated at 110–120 rpm for 7–9 minutes and stopped, incubated for 40 minutes at 39° C., and standed at room temperature for 90 minutes;

5. the above material was filteredg with clean silk cloth, discarded the filtrate, soaked in distilled water for 15 hours, dried at 65° C. for 28 hours to obtain 2.2367 g medicament of 1-calcium phosphate-uracil as white crystal or crystalline powder. The structure formula of medicament was showed in FIG. 1.

Example 3

A Method for the Preparation of the Medicament of 1-calcium Phosphate-uracil, Comprising Following Steps 1. phosphoric acid working solution was prepared: 40 g of $Na_2HPO_4.12H_2O$ was mixed with 4.022 ml of 85% aqueous $H_3PO_4$ solution, the pH of mixed solution was controlled to 6.1;
2. 4 g uracil was added to 1200 ml of said phosphoric acid working solution for dissolution, obtained solution was poured into reactor, the reactor was disposed in a water tank of 39° C. without contacting with water, 32 mg of creatine kinase, i.e. CPK with a code of 2.7.3.2 was added, agitated at 120 rpm for 60 minutes and stopped, incubated for 30 minutes, and standed at room temperature for 30 minutes;
3. the above solution was filtered with filter, the all of 1175 ml filtrate obtained was poured into reactor, and disposed in a water tank of 39° C.;
4. 43 ml of 5% aqueous $CaCl_2$ solution was added, agitated at 180 rpm for 15 minutes, then agitated at 120 rpm for 8 minutes and stopped, incubated for 40 minutes at 39° C., and standed at room temperature for 80 minutes;
5. the above material was filtered with clean silk cloth, discarded the filtrate, soaked in distilled water for 15 hours, dried at 55–65° C. for 24 hours to obtain 2.1716 g medicament of 1-calcium phosphate-uracil as white crystal or crystalline powder. The structure formula of medicament is showed in FIG. 1.

Example 4

Figure 2:
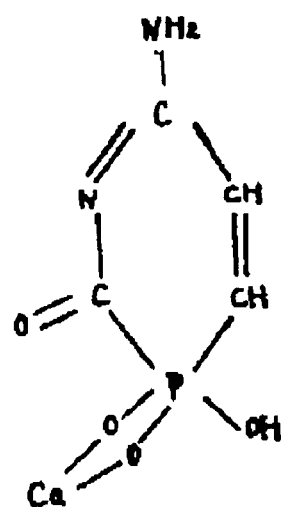
FIG. 2 shows structure formula of 1-calcium phosphate-cytosine.

Preparation of 1-calcium Phosphate-cytosine (FIG. 2)

Analogous to the method of Example 1, 1-calcium phosphate-cytosine was prepared, wherein position 1 of the pyrimidine was substituted with $H_3PO_4$.

Example 5

Figure 3:
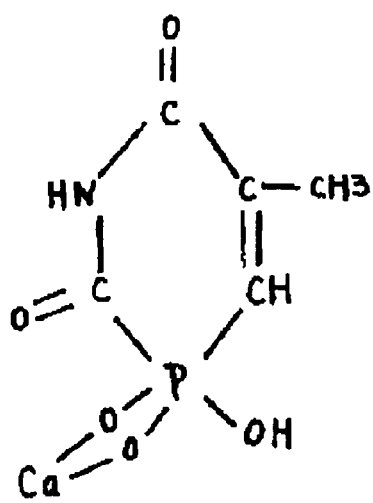
FIG. 3 shows structure formula of 1-calcium phosphate-thymine.

Preparation of 1-calcium Phosphate-thymine (FIG. 3)

Analogous to the method of Example 1, 1-calcium phosphate-thymine was prepared, wherein position 1 of the pyrimidine was substituted with $H_3PO_4$.

Example 6

Figure 4:
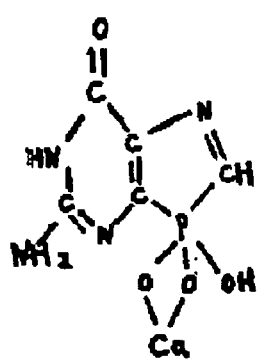
FIG. 4 shows structure formula of 9-calcium phosphate-guanine.

FIG. 4: Preparation of 9-calcium Phosphate-guanine (FIG. 4)

Analogous to the method of Example 1, 9-calcium phosphate-guanine was prepared, wherein position 9 of the purine was substituted with $H_3PO_4$.

Example 7

Figure 5:
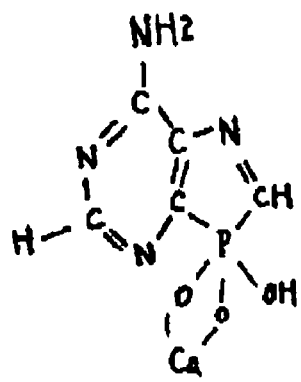
FIG. 5 shows structure formula of 9-calcium phosphate-adenine.

Preparation of 9-calcium Phosphate-adenine (FIG. 5)

Analogous to the method of Example 1, 9-calcium phosphate-adenine was prepared, wherein position 9 of the purine was substituted with $H_3PO_4$.

Example 8

Figure 6:
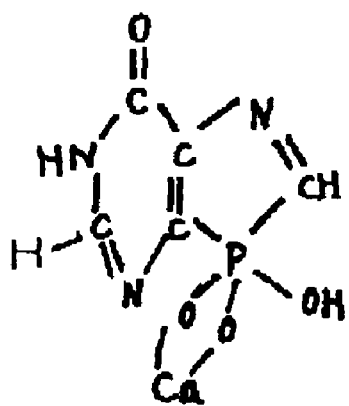
FIG. 6 shows structure formula of 9-calcium phosphate-hypoxanthine.
Figure 7:
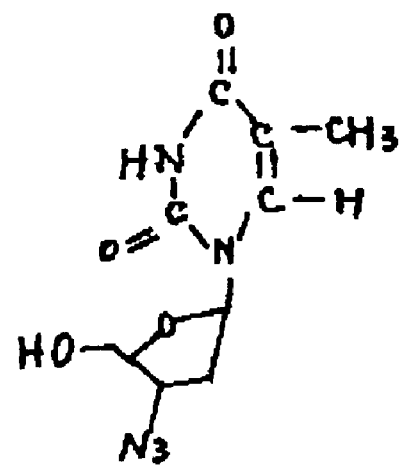
FIG. 7 shows structure formula of anti-AIDS drug AZT azidothymidine zidovudine of prior art.
Figure 8:
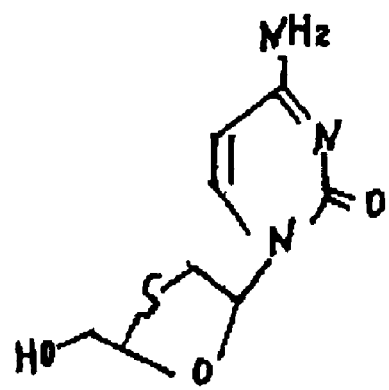
FIG. 8 shows Structure formula of anti-AIDS drug 3Tc lamivudine of prior art.

Preparation of 9-calcium Phosphate-hypoxanthine (FIG. 6)

Analogous to the method of Example 1, 9-calcium phosphate-hypoxanthine was prepared, wherein position 9 of the purine was substituted with $H_3PO_4$.

Clinical Examples

Therapeutic Effect of the Medicament of 1-calcium Phosphate-uracil

Case 1

A 47 years old woman, who had been suffering from a continued bad cough for 2 months and not susceptive to antibiotics therapy, was administrated orally with medicament of 1-calcium phosphate-uracil for 5 days, 15 mg per day.

Therapeutic effect: The symptom of cough was cured completely, and the symptom of incontinence of urine disappeared at the same time.

Case 2

A 78 years old man, who had been suffering from cough for about 50 years and hyperplasia of prostate for 7 years and recently relapsed into continued cough for 15 days and constipation, was administrated orally with medicament of 1-calcium phosphate-uracil for 5 days, 15 mg per day.

Therapeutic effect: cough symptom was alleviated, constipation disappeared and the frequency of nocturia decreased significantly.

Case 3

A 20 years old man, who had caught a cold and had a fever of 39° C., was administrated orally with medicament of 1-calcium phosphate-uracil for 1 day, 15 mg per day.

Therapeutic effect: fever was allayed after 1 day and symptom of cough disappeared after 2 days.

Case 4

A 21 years old woman, who had a fever of 40.5° C., was administrated orally with medicament of 1-calcium phosphate-uracil for 1 day, one time per day, 15 mg each time.

Therapeutic effect: fever was allayed after 1 day and symptom of cough disappeared after 3 days.

Case 5

During the period of influenza taking place at Chengdu in December, 2001, 2 persons among 8 persons in an undergraduate dormitory of Sichuan Normal University was administrated orally in advance with medicament of 1-calcium phosphate-uracil for 1 day, one time per day, 15 mg each time, and consequently were not infected with influenza; all of other 6 persons, however, were infected with influenza because of not being administrated in advance with medicament of 1-calcium phosphate-uracil. One day after infection, 2 of 6 infected persons were administrated orally with medicament of 1-calcium phosphate-uracil for 3 day, one time per day, 15 mg each time. Therapeutic effect: fever was allayed after 1 day and symptom of cough faded away after 3 days. Instead of being administrated with medicament of 1-calcium phosphate-uracil, the other 4 infected persons were treated according to conventional therapeutic regimen, recovered until after 15 days.

Case 6

4 persons, who had suffered from constipation for about 10 years, defecated 1–2 times a week when administrated with conventional drugs. After oral administration of medicament of 1-calcium phosphate-uracil for 1 day, one time per day, 12 mg~15 mg each time, they defecated smoothly, once a day.

Case 7

A 43 years old woman, who had suffered from frequent premature beat, cardiac distress for 3 years and constipation for 5 years, was administrated orally with medicament of 1-calcium phosphate-uracil for 20 days, 13 mg per day.

The therapeutic effect: the symptoms of palpitation premature beat and cardiac distress disappeared completely after 20 days from administration and constipation symptom disappeared after 1 day from administration.

Case 8

The medicament can ameliorate sleeping and supplement stamina. 20 persons aging 12~70 years old were tested and administrated for only one day, 15 mg per day, and had a good sleeping on the same day and all of them were full of vigor in the next day.

Case 9

A 65 years old man, who suffered liver cancer in a most serious stage, was administrated orally with medicament of 1-calcium phosphate-uracil for 10 months, one time per day, 15 mg each time.

Therapeutic effect: liver tumor was disappeared upon the examination of CT.

What is claimed is:

1. A compound of 1-calcium phosphate-uracil, of a structure of the following formula:

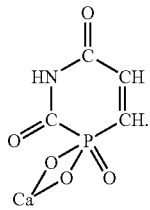

2. The compound according to claim 1 which is a flavourless, white crystal or crystalline powder with a molecular weight of 216.1276.

3. A 1-calcium phosphate-cytosine compound of a structure of the following formula:

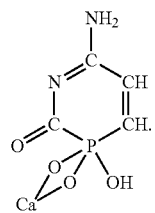

4. A 1-calcium phosphate-thymine compound of a structure of the following formula:

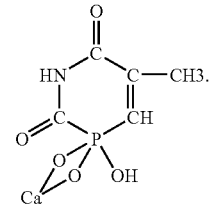

* * * * *